(12) United States Patent
Maertz (10) Patent No.: US 9,153,143 B2
(45) Date of Patent: Oct. 6, 2015

(54) HOT TOWELS

(76) Inventor: Richard James Maertz, Laguna Hills, CA (US)

( * ) Notice: Subject to any disclaimer, the term of this patent is extended or adjusted under 35 U.S.C. 154(b) by 809 days.

(21) Appl. No.: 13/366,077

(22) Filed: Feb. 3, 2012

(65) Prior Publication Data

US 2013/0199557 A1 Aug. 8, 2013

(51) Int. Cl.
| | |
|---|---|
| G09B 19/00 | (2006.01) |
| A47K 10/32 | (2006.01) |
| A61F 7/03 | (2006.01) |
| A61L 2/18 | (2006.01) |
| A61F 7/02 | (2006.01) |

(52) U.S. Cl.
CPC ............ *G09B 19/0076* (2013.01); *A47K 10/32* (2013.01); *A61F 7/034* (2013.01); *A47K 2010/3273* (2013.01); *A61F 2007/0276* (2013.01); *A61L 2/18* (2013.01)

(58) Field of Classification Search
CPC combination set(s) only.
See application file for complete search history.

(56) References Cited

U.S. PATENT DOCUMENTS

| | | | |
|---|---|---|---|
| 3,632,516 A | 1/1972 | Antonelli | |
| 3,957,472 A | 5/1976 | Donnelly | |
| 4,110,426 A | 8/1978 | Barnhurst | |
| 4,425,251 A | 1/1984 | Gancy | |
| 4,573,447 A | 3/1986 | Thrash | |
| 5,114,507 A | 5/1992 | Piltz | |
| 6,547,468 B2 | 4/2003 | Gruenbacher | |
| 6,752,998 B2 | 6/2004 | Verdrel-Lahaxe | |
| 7,476,047 B2 * | 1/2009 | Brunner et al. | 401/134 |
| 7,651,290 B2 * | 1/2010 | Bauer et al. | 401/133 |
| 7,967,140 B2 | 6/2011 | Grossman | |
| 8,051,979 B2 | 11/2011 | Smith | |
| 8,104,986 B2 * | 1/2012 | Nash | 401/132 |
| 2011/0042257 A1 | 2/2011 | Mueller | |

OTHER PUBLICATIONS

Centers for Disease Control and Prevention; "Handwashing: Clean Hands Save Lives"; CDC 24/7: Saving Lives, Protecting People, Saving Money through Prevention; Jul. 25, 2011; US Department of Health and Human Services; Atlanta, GA.
Stone, S.P.; "Hand hygiene—the case for evidence-based education" Journal of the Royal Society of Medicine; Jun. 2001; p. 278-281; vol. 94, Academic Department of Geriatric Medicine, Roayl Free Campus, Royal Free and University College Medical School, London.
Centers for Disease Control and Prevention; Stop Germs! Stay Healthy! Wash Your Hands!; CDC 24/7: Saving Lives, Protection People, Saving Money through Prevention; Jul. 15, 2008; US Department of Health and Human Services: Atlanta, GA.
Centers for Disease Control and Prevention; "After you touch ducklings or chicks, wash your hands so you don't get sick!"; CDC 24/7: Saving Lives, Protecting People, Saving Money through Prevention; 2008; US Dept. Health Human Serv; Atlanta,GA.

(Continued)

*Primary Examiner* — David Walczak
(74) *Attorney, Agent, or Firm* — Patnstr, APC; Tom Brody; Peter Jon Gluck (57) ABSTRACT

Personal portable devices may, in certain aspects, include at least two compartments, where one compartment comprises a substrate, such as a towel, and the other compartment contains a solvent, such as an anti-microbial solvent or cleansing solvent, where the device introduces or impregnates the solvent into the substrate, and where the substrate of the device can be heated.

18 Claims, 5 Drawing Sheets

(56) References Cited

OTHER PUBLICATIONS

US Dept of Health and Human Services; "Don't let what happened to me happen to you. Protect People Everywhere: Wash Your Hands, Use Gloves or Utensils, and Never Work When Your Are Sick"; U.S. Food and Drug Administration; Silver Spring, MD.
Lee, Marilyn B.; "A review of enteric outbreaks in Child Care Centers: effective infection control recommendations"; Journal of Environmental Health; Oct. 1, 2008; 71(3):24-32; National Environmental Health Association; Denver, CO.
Lennell, Anne et al; "Alcohol-based hand-disinfectin reduced children's absence from Swedish day care centers"; Acta Paediatrica Promoting Child Health; Sep. 2008: p. 1672-1680; vol. 97:12; Örebro University Hospital; Örebro, Sweden.
Cannon, Michael J., et al; "Washing our hands of the congenital cytomegalovirus disease epidemic"; BioMed Central Public Health Journal; Jun. 20, 2005; p. 1-8; vol. 5:70; BioMed central Ltd., London, UK.
Thompson; "Infectious Diarrhea in children: Controlling transmission in the child care setting"; Journal of Paediatrics and Child Health, Jun. 1994, p. 210-219, vol. 30, Blackwell Scientific Publications, Melbourne, Australia.
Mallet, Pascal, et al; "Rating and Recognition of Peers' Personal Odors by 9-Year-Old Children: An Exploratory Study" The Journal of General Psychology; 1998; p. 47-64; vol. 125 (1); Taylor & Francis, Inc.; Philadelphia, PA.
Dematte, M. Luisa; "Olfactory cues Modulate Facial Attractiveness"; Chemical Senses (Journal); May 16, 2007; p. 603-610; vol. 32; Oxford Unviersity Press; Oxford, UK.
Popp, Roland, et al; "Olfactometry in fMRI studies: odor presentation using nasal continuous positive airway pressure"; ACTA Neurobiologiae Experimentalis; 2004; p. 171-176; vol. 64; University of Regensburg; Regensburg, Germany.
Brattoli, Magda, et al; "Odour Detection Methods: Olfactometry and Chemical Sensors"; Sensors (Journal); May 16, 2011; p. 5290-5322; vol. 11; Molecular Diversity Preservation International (MDPI) AG; Basel, Switzerland.
Cometto-Muniz, J. Enrique; "Structure-activity relationsips on the odor detectability of homologous carboxylic acids by humans"; Experimental Brain Research; Oct. 8, 2010; p. 75-84; vol. 207; Springer Verlag; Heidelberg, Germany.
Zaviacic, M.;"Cosmetic perfumes vs. human pheromones (natural chemical scents) of the human female and male in signalling and performing context of their sexual behaviour" Bratisl Lek Listv: 2009;p. 472-475; vol. 110(8); Slovakia Publishina House; Slovakia.
Hoosain, Sheikh Julfikar; "Potentiation of the Ionotropic GABA Receptor Response by Whiskey Fragrance"; Journal of Agricultural and Food Chemistry; 10/042002, p. 6828-6834; vol. 50; American Chemical Society; Washington, D.C.
Hoosain, Sheikh Julfikar; "Effects of Tea Components on the Response of GAGA Receptors Expressed in Xenopus Oocytes"; Journal of Agricultural and Food Chemistry; May 31, 2002; p. 3954-3960; vol. 50; American Chemical Society; Washinaton, D.C.
Hossain, Sheikh Julfikar; "Effects of Coffee Components on the Response of GABA Receptors Expressed in Xenopus Oocytes"; Journal of Agricultural and Food Chemistry; Nov. 21, 2003; p. 7568-7575; vol. 51; American Chemical Society; Washington, D.C.
Ye, Tao, et al; "Can odors of TCM be captured by electronic nose? The novel quality control method for musk by electronic nose coupled with chemometrics"; Journal of Pharmaceutical and Biomedical Analysis; 2011; p. 1239-1244; vol. 55; Elsevier, Holland.
Dematte, M. Luisa; "Cross-Modal Interactions Between Olfaction and Touch"; Chem. Senses; 2006; p. 291-300; vol. 31; Oxford Unviersity Press; Oxford, UK.
Vance, et al; "Evaluation of the antimicrobial efficiency of green tea extract against streptococcus pyogenes in vitro"; Biomedical Sciences Instrumentation; Apr. 2011; p. 177-182; vol. 47: Instrument Society of America; Research Triangle Park, North Carolina.
Field, Tiffany; "Lavender Fragrance Cleansing Gel Effects on Relaxation"; International. Journal of Neuroscience; 2005; p. 207-222; vol. 115; Taylor & Francis Inc. , UK.
Redd, William H.; "Frangrance Administration to Reduce Anxiety during MR Imaging"; Journal of Magnetic Resonance Imaging; 1994; p. 623-626; vol. 4; Elsevier; Amsterdam.
Herz, Rachel S.; "Are Odors the Best cues to Memory?"; Annals of the New York Academy of Sciences; Nov. 1998; p. 670-674; vol. 855; Wiley-Blackwell on behalf of New York Academy of Sciences; Hoboken, New Jersey.
Herz, Rachel S.; "Neuroimaging evidence for the emotional potency of odor-evoked memory"; Neuropsychologia; 2004; p. 371-378; vol. 42; Elsevier; Holland.
Jehl, Christine, et al; "Developmental effects on odor learning and memory in children"; Annals of the New York Academy of Sciences; 1998; p. 632-634; vol. 855; Wiley-Blackwell on behalf of New York Academy of Sciences; Hoboken, New Jersey.
Seo, Han-Seok, et al; "Cross-modal integration between odors and abstract symbols"; Neuroscience Letters; Jul. 12, 2010; p. 175-178; vol. 478(3); Elsevier, Holland.
Rossi; "Distinct olfactory cross-modal effects on the human motor system"; Plos One; Feb. 27, 2008; p. 1-9; vol. 3:2:e1702; Public Library of Science; USA.
Darnaud, Raquel, et al; "Health Education in schools in Argentina: an art contest as motivating activity"; Pan American Journal of Public Health; Feb. 2009; p. 181-187; vol. 25(2); Pan American Health Organization; Washington, D.C.
Jabre, Bushra; "Innovative approaches in nutrition education in the Pacific region"; International Journal of Health Education; 1981; p. 95-101; vol. 24(2); International Union for Health Education; Geneva/Paris/USA.
Hughes, Kristine; The Writer's Guide to Everyday Life in Regency and Victorian England from 1811-1901; Feb. 15, 1998; cover page; Writer's Digest Books; United States.
Post, Peggy, et al; "Emily Post's Etiquette, 18th Edition"; 2011; Harper Collin's Publisher, New York.

\* cited by examiner

HOT TOWELS

FIELD OF THE DISCLOSURE

The disclosure relates to systems, devices, and methods for cleansing hands. In particular, the disclosure provides compartmented devices having internally disposed substrates or towels, in combination with antimicrobial agents or cleaning agents.

BACKGROUND OF THE DISCLOSURE

Hand washing prevents the spread of germs and disease. Improved hand hygiene can prevent illnesses, as can prevent spreading of germs and illnesses to others (see, e.g., Center for Disease Control and Prevention. Handwashing: Clean Hands Save Lives; U.S. Department of Health and Human Services in 2010). Early evidence of clinical benefit from hand hygiene became available from work by Semmelweiss (see, e.g., Stone (2000) Hand hygiene—the case for evidence-based education. J. Royal Society Med. 94:278-281). Situations especially critical for hand cleansing include food preparation at home or in restaurants, caring for sick persons, treating wounds, the context of discharging metabolic endproducts, changing soiled undergarments of infants, and handling ducklings and chicks (see, e.g., Stop Germs! Stay Healthy! Wash Your Hands by U.S. Dept. of Health and Human Services, Centers for Disease Control and Prevention (1 page) (accessed Jan. 21, 2012); After You Touch Ducklings or Chicks, Wash Your Hands So You Don't Get Sick! by U.S. Dept. of Health and Human Services, Centers for Disease Control and Prevention (1 page) (accessed Jan. 21, 2012); Don't Let What Happened to Me, Happen to You by U.S. Dept. of Health and Human Services, Centers for Disease Control and Prevention (1 page) (accessed Jan. 21, 2012).

Cleansing of hands by hand-disinfectants, by children and staff of daycare centers has been shown to mitigate outbreaks and to reduce absenteeism (see, e.g., Lee and Greig (2008) J. Environ. Health. A review of enteric outbreaks in child care centers: effective infection control recommendations. 71:24-32; Kuhlmann-Berenzon et al (2008) Alcohol-based hand-disinfection reduced children's absence from Swedish day care centers. Acta Paediatr. 97:1672-1680). Cleansing hands has also been shown to reduce the incidence of viral infections, as well as bacterial infections (see, e.g., Cannon and Davis (2005) Washing our hands of the congenital cytomegalovirus disease epidemic. BMC Public Health. 5:70; Thompson (1994) Infectious diarrhea in children: controlling transmission in the child care setting. J. Paediatr. Child Health. 30:210-219).

Bacteria, viruses and germs live on surface areas, such as: counter tops, faucets, tabletops, toys, stoves, sinks, refrigerators, door knobs, and the like. The present disclosure can be used to clean hands and wipe down surfaces that are frequently touched by children.

Hand sanitizers have become a surrogate for hand washing. However, hand sanitizers may be less effective than the present disclosure because not all hand sanitizers contain the 60% alcohol necessary to effectively kill germs; hand sanitizers may not be as effective as soap and warm water; and because hand sanitizers may not effectively penetrate grease and oils.

The long standing need for portable personal hygienic systems have not been fully addressed. The present disclosure provides a mobile hand washing device which overcomes certain drawbacks of conventional hand washing or hand cleansing regimes.

SUMMARY OF THE DISCLOSURE

The disclosure provides a portable system for personal hygiene that comprises, in combination, a first compartment configured for containing a substrate, a second compartment configured for containing a solvent, wherein one or both compartments comprise a frangible region that can be opened or ruptured, wherein opening or rupturing the frangible region allows the solvent to contact and absorb into the at least one substrate, where maintaining the frangible region prevents the solvent from contacting the at least one substrate, and further comprising a member that is manually operable by user that opens or ruptures the frangible region. Also provided, is the above system, wherein the first compartment contains at least one substrate; or wherein the substrate is at least one absorbent towel; or wherein the first compartment does not contain a substrate; or wherein the second compartment contains at least one solvent; or wherein the solvent comprises water or an organic solvent, or a mixture of water and an organic solvent; or wherein the solvent comprises at least one fragrant compound, at least one anti-microbial compound, or a combination of fragrant and anti-microbial compounds; or wherein the solvent comprises at least one fragrant compound that is a child-oriented fragrant compound or an adult-oriented fragrant compound; or wherein the second compartment does not contain a solvent; or wherein the second compartment comprises a capsule, where the capsule is configured for containing the solvent. In another aspect, what is provided is the above system, wherein the first compartment contains a first chemical reagent of an exothermic composition, and the second compartment contain a second chemical reagent of the exothermic substance, wherein combination of the two reagents generates heat, wherein the frangible region is configured, when opened or ruptured, to allow combination of the two reagents to create an exothermic reaction, and wherein at least one of the compartments contains a solvent, where the exothermic reaction increases the temperature of the solvent (without any limitation to degree increase), or an increase in temperature by at least five degrees centigrade, by at least ten degrees, by at least 15 degrees, by at least 20 degrees, by at least 25 degrees, by at least 30 degrees, and the like.

What is also embraced, is the above system, wherein the system is configured so that, in use, the first chemical reagent, the second chemical reagent, and the exothermic substance do not touch or mix with the solvent and do not touch or absorb into the substrate. Furthermore, what is provided is the above system, wherein the first compartment comprises a third compartment, or wherein the second compartment comprises a fourth compartment, wherein the third compartment is configured for containing the first chemical reagent, and the fourth compartment is configured for containing the second chemical reagent.

In another aspect, what is provided is the above system, wherein the second compartment that is configured for containing a solvent comprises at least one capsule, wherein the at least one capsule contains essentially all of the solvent that is comprised by the second compartment. In yet another embodiment, what is provided is the above system, wherein the first compartment, second compartment, or both first and second compartments, comprise an adhesive strip or pull-cord that is operably linked to the frangible region, wherein in use, the adhesive strip or pull-cord opens or ruptures the frangible region. Also embraced, is the above system, wherein the first compartment and the second compartment are configured to define a chamber that is entirely in between the first and second compartments, wherein in use opening or rupture of the frangible region results in solvent leaving the second compartment for the chamber, and solvent in the chamber entering the substrate compartment.

Methods embodiments are also contemplated. What is provided is a method for cleaning hands, comprising opening or rupturing the frangible region of the system as set forth above, allowing solvent to contact and absorb into the at least one substrate, withdrawing the at least one substrate from the system, and applying or wiping the at least one substrate to a hand.

Also provided is a method for eliciting a recall of a procedure for cleaning hands, or for motivating a child to clean his or her hands, comprising the method as set forth above, wherein the solvent comprises a child-oriented fragrant compound, wherein, in use, the fragrant compound is absorbed by the substrate, and wherein, in use, the fragrant compound that is absorbed by the substrate is detectable by a child holding the substrate at a distance of less than two inches, less than three inches, less than five inches, less than eight inches, or less than one foot from the child's own nose, and the like.

What is further contemplated is the above method, wherein the eliciting recall is measurable by a first test, and the motivating a child is measurable by a second test, wherein the first test or second test are one of a psychological test, behavioral test, electroencephalogram test, or brain magnetic resonance imaging (MRI) test.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

DETAILED DESCRIPTION

Figure 1:
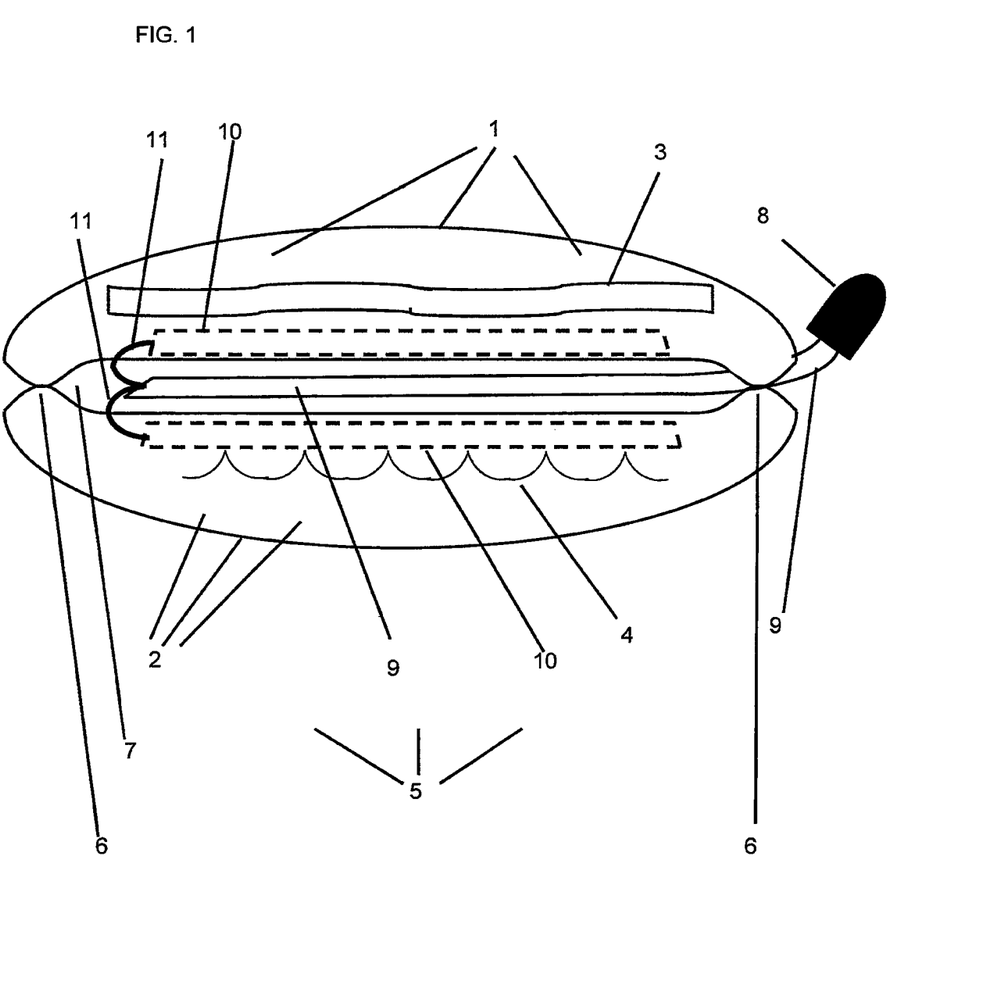
FIG. 1 provides a cross-sectional view of device with pull-tab operably linked with two strips.

FIG. 1 shows a first compartment (1) and a second compartment (2), where first compartment contains a substrate (3), such as one or more towels (3), and where second compartment (2) contains a solvent (4), such as solvent comprising an anti-microbial compound (4), or a solvent comprising an anti-microbial compound (4) in combination with a fragrant compound (4). A stylized, non-limiting version of the substrate is shown. A stylized version of solvent is shown by a pattern of waves (linked sinusoidal curves).

First compartment (1) and second compartment (2) are sealed by a sealing or attachment means (6). In some embodiments, the sealing means is configured to maintain attachment of the first compartment (1) and the second compartment (2), and to create a chamber (7), where the chamber is sandwiched in between the first compartment (1) and second compartment (2). FIG. 1 shows a cross section view of the device or system, which reveals an "x-ray vision" diagram of substrate (3) and solvent (4). Sealing means encompasses, without limitation, glue, adhesive, heat-melting, staples, stitches, an intermediary sealing structure such an annular structure or gasket, or manufacture of compartment (1) and compartment (2) as a unitary structure (in which case there may not be any need, e.g., for glue or heat-sealing.

Regarding the three dimensional conformation of the device or system, first compartment can be substantially in a first plane and second compartment can be substantially in a second plane, in the manner of two pieces of bread in a sandwich that contains minimal filling. Alternatively, the sandwich can be rolled into a cylinder, or rolled into a spiral, providing cylindrical or spiral embodiments. Also provided are co-axial embodiments, where one compartment is a central cylinder (or other shape) and a second compartment is an outer cylinder (or other shape). Spherical embodiments are also provided, where one compartment is an inner sphere and other compartment is an outer sphere.

FIG. 1 also reveals a pull-tab (8) that is operably linked with a pull-strip (9) (or pull-string; pull-wire; pull-ribbon), where the pull-strip (9) is operably linked to one or more adhesive strips (10). The one or more adhesive strips (10) is configured to create an opening in the first compartment (1) and an opening in the second compartment (2), where the openings allow the solvent (4) to adsorb to the surface of substrate (3), to absorb into the matrix of substrate (3), or to impregnate substrate (3). Structure (7) is chamber. In alternate embodiments, the two compartments can be situated flush to each other, where there is little or no chamber, or where there does not exist any chamber. Structure (11) refers to an operable connection between pull-strip (9) and adhesive strip (10). Structure (11) can be continuous with and indistinguishable from pull-strip (9), or it can be continuous with and indistinguishable from adhesive strip (10), or structure (11) can be distinct from (9) and from (10). Structure (5) indicates the overall device or system. Pull-tab (8) can be a structure that is operably linked with pull-strip (9), but where it is distinct from pull-strip (9). Alternatively, pull-tab (8) can be continuous with, integral with, of unitary construction with, or made of the same material, as pull-strip (9).

The chamber and seal in FIG. 1, and a corresponding chamber, chambers, seal, or seals, in other figures, can be configured to be airtight, to resist water leakage, to maintain physical proximity of the first compartment and second compartment, or to maintain physical proximity of the first and second compartments without being airtight or without resisting water leakage. Airtightness can be measured, for example, by subjecting system or device to air pressure or to the vacuum that can be created by an adult forcibly exhaling or inhaling, respectively, or to a pump. The seal can resist, for example, up to 10, 20, 30, 40, 50, 60, 70, 80, 90, 100, 125, 150, 175, 200, 225, 250, 275, or 300 centimeters of mercury, when vacuum is applied to outside of device, or when pressure is introduced into chamber by way of airtight tube, where pressure is measured by a manometer (see, e.g., Dwyer Instruments, Inc., Michigan City, Ind.; W.W. Grainger, Inc., Lake Forest, Ill.).

Figure 2:
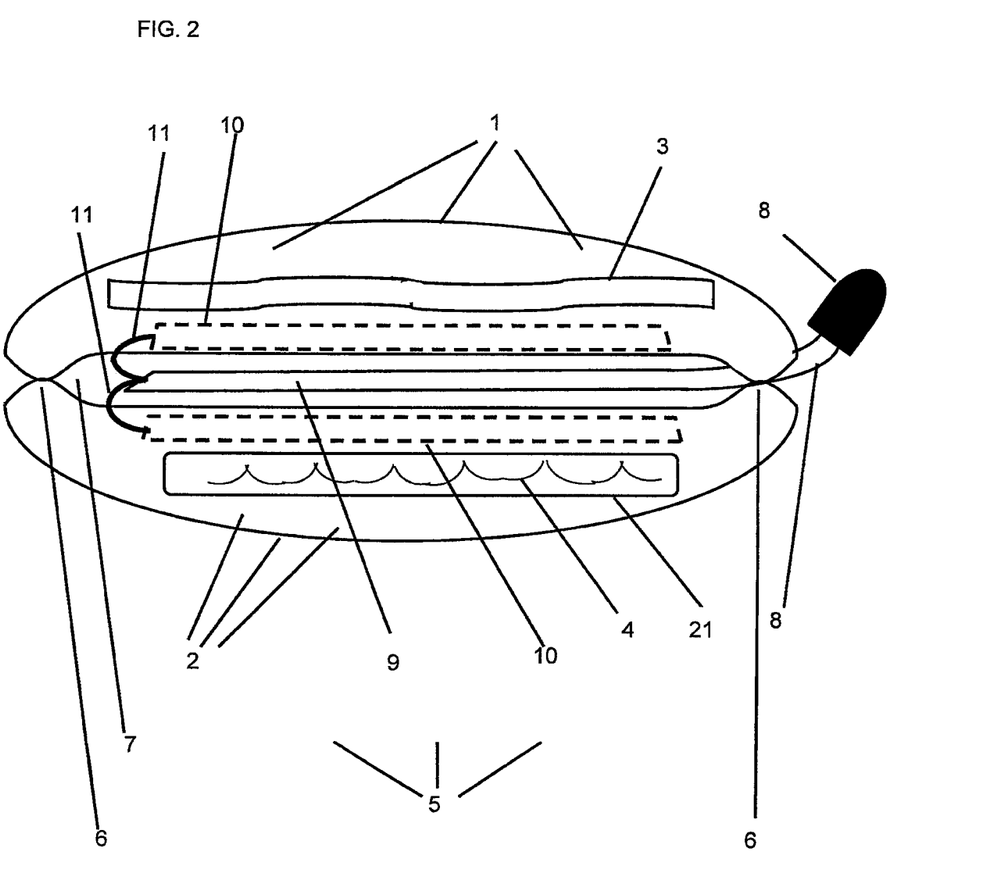
FIG. 2 illustrates a cross-sectional view of device with pull-tab operably linked with two strips, where one of the compartments comprises a capsule.

FIG. 2 identifies equivalent structures as in FIG. 1, but in FIG. 2, compartment (2) encloses a capsule (21) that contains solvent (4). In FIG. 2, the pull-strip (9) is operably linked to the adhesive strip (10) of compartment (1) and also operably linked to the adhesive strip (10) of compartment (2). The skilled artisan will readily perceive which adhesive strip in the figure is operably linked with compartment (1) and which is operably linked with compartment (2). The device or system can include one or more capsules. Without limitation, the capsule can have the shape of a circle, cylinder, cylinder with rounded edges, teardrop, heart, triangle, string of beads where each bead is in fluid communication with all other beads, and the like. In some embodiments of the device or system, the capsule is transparent or translucent, where the device or system is configured so that a substantial part of the transparent or translucent part of the capsule is visible to the consumer, that is, prior to opening any part of the system or device, for example, prior to pulling the pull-tab.

Figure 3:
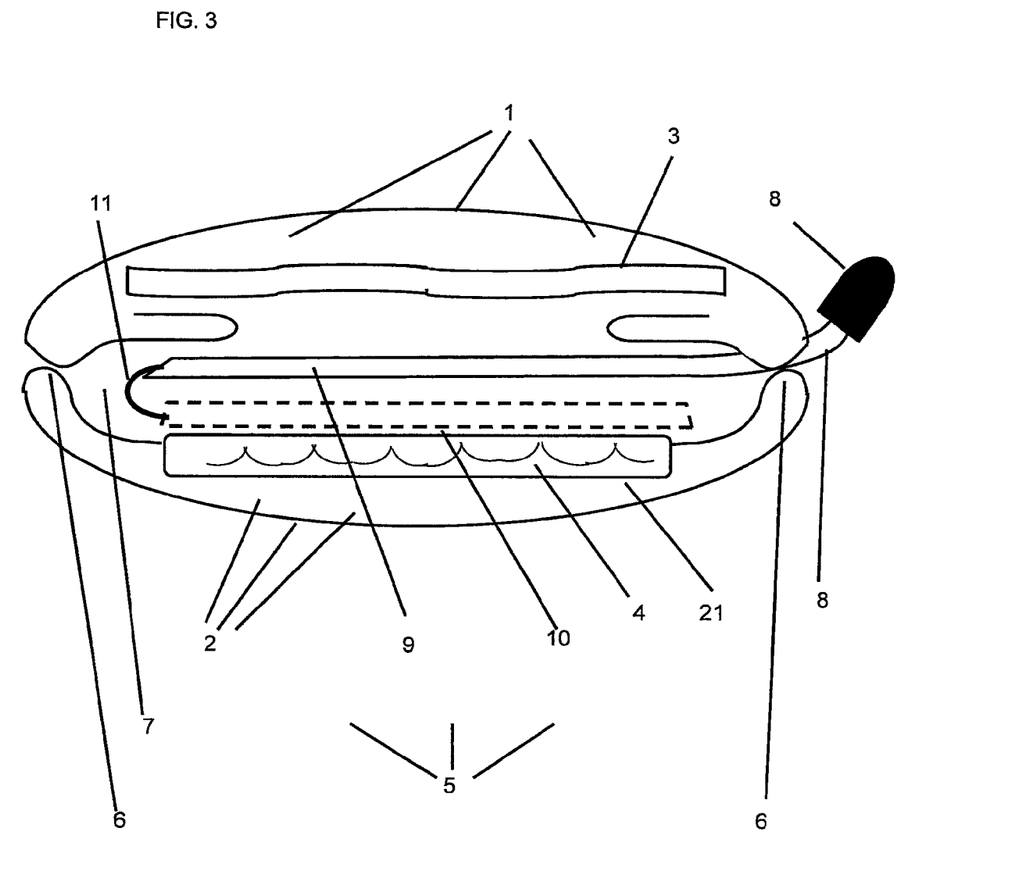
FIG. 3 shows a cross-sectional view of device with pull-tab operably linked with one strip, where one of the compartments comprises a capsule.

FIG. 3 provides an embodiment where compartment (1) that contains substrate (3) is open and does not need opening by way of a pull-tag, pull-strip, or adhesive strip. Even though compartment is open, the compartment partially surrounds substrate (e.g., towel) sufficiently to maintain the towel in a stable position in compartment (1), or in a position that facilitates efficient impregnating of solvent into towel. In FIG. 3, the pull-tab and adhesive strip is used to open up capsule (21). The adhesive strip is shown with a dashed line only to distinguish it from the pull-strip. Without intending any limitation, the FIG. 3 embodiment, compartment (1) contains a lip or shelf that maintains substrate in a stable position.

Figure 4:
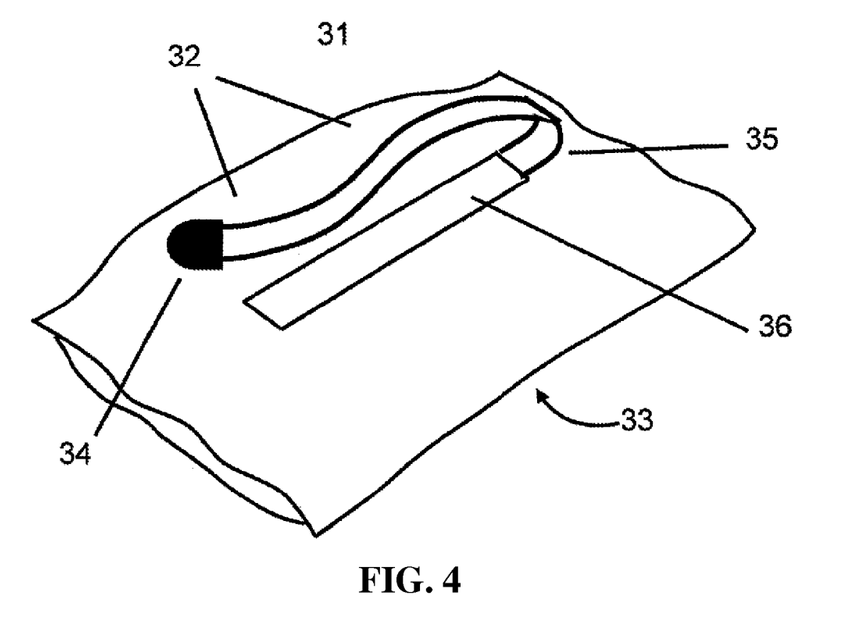
FIG. 4 provides a three-dimensional view of a compartment and strip.

FIG. 4 illustrates, without limitation, a compartment (31), with first face (32), second face (33), pull-tab (34), pull-strip (35), and adhesive strip (36). The pull-tab and pull-strip can be made of a single, uniform unit; that is, made of the same substance with the same color, same texture, same width, and same thickness. Alternatively, the pull-tab and pull-strip can be distinguished from each other in terms of, e.g., substance (e.g., type of plastic polymer), color, texture, width, thickness, and the like. The adhesive strip shields a predetermined opening in compartment (31), where the opening can be pre-cut in the form of a slit (or plurality of slits) or in the form of one or more holes (not shown), where the opening can comprise perforations, a frangible, leakproof region, and the like. In some aspects, adhesive strip shields a frangible region that is airtight or watertight, and which does not contain any pre-formed opening, but where removing adhesive strip has two effects: (1) Creating a de novo opening in frangible region; and (2) Unshielding the area where the opening is being created. The pull-tab and pull-strip can be folded back over the entire longitudinal axis of the adhesive strip (36), to facilitate initiation of peeling of the adhesive strip from the first face (32). Where compartment (31) contains a towel, and where there is only one hole (not shown), the hole can be dimensioned to be about 5%, about 10%, about 20%, about 30%, about 40%, about 50%, about 60%, about 70%, about 80%, about 90%, about 100%, about 125%, about 150%, or about 200%, the dimension of a towel that is confined in compartment (31), for example, dimensions that are a width and length.

Figure 5:
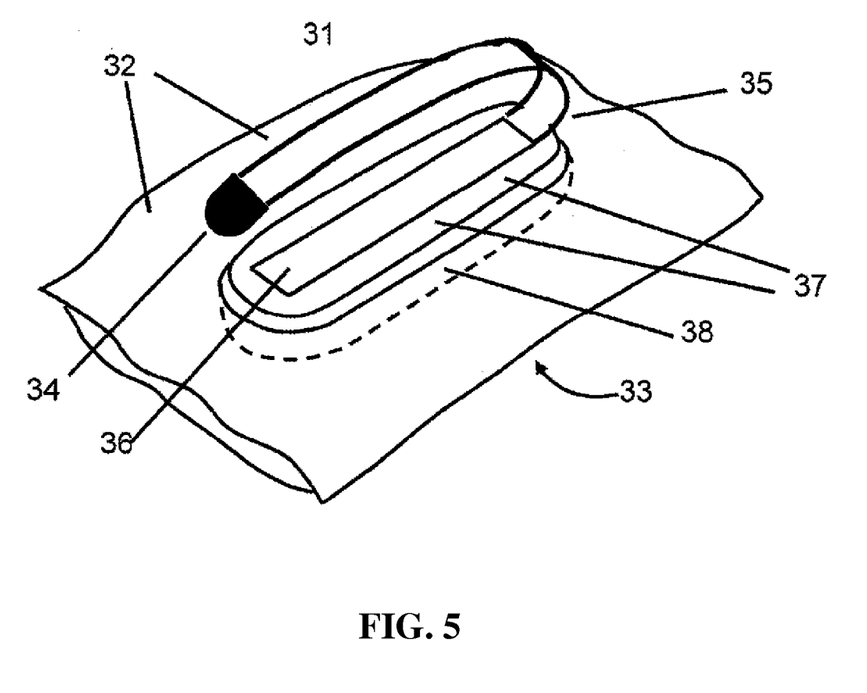
FIG. 5 shows a device comprising a compartment, a strip, and a capsule

FIG. 5 illustrates, without limitation, compartment (31), with first face (32), second face (33), pull-tab (34), pull-strip (35), and adhesive strip (36), capsule (37), and region of capsule (38) situated beneath surface of first face (32). Capsule can reside entirely on the surface of first face (32) of compartment (31) or, as shown in FIG. 5, capsule can reside partially above and partially below first face (32). In embodiments, capsule (37) is transparent or translucent to visible light, where compartment (31) is configured in the present system, device, or method, so that consumer holding the system or device can see the color or texture of the material within the capsule, e.g., dye, sparkles, glitter, particles, strands, or threads, and where these are suspended or dispersed in fluid, solvent, or gel.

In FIG. 4, the adhesive strip covers a frangible region, where the frangible region encompasses, without intending any limitation, a slit, a perforated slit, a scored region with angled scores, a scored region with a single longitudinal score, a weakened region comprising material that is relatively thin, a single hole having smaller dimensions than the strip and that therefore can be sealingly covered by the strip, a plurality of holes that is sealingly covered by the strip, and the like. In this context, frangible encompasses regions of compartment that are already open, even where consumer's activity in removing the adhesive strip does not appreciably cause any further opening of the frangible region.

Where the compartment (31) contains a capsule (37), and where part of the capsule extends beyond a plane that is defined by the first face (32), for example, in the form of a bubble, the compartment (31) is defined as comprising the entire capsule.

Figure 6:
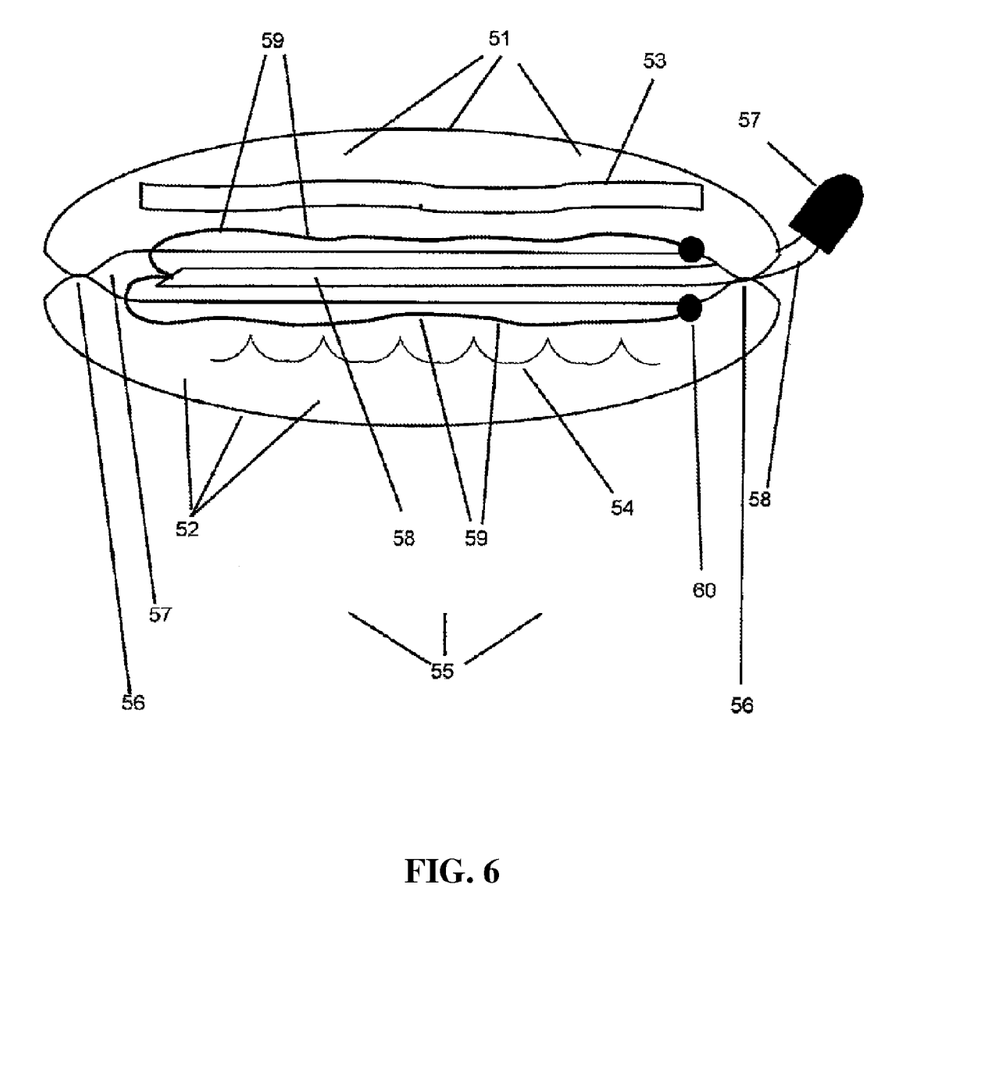
FIG. 6 is a cross-sectional view of device, where pull-tab is operably linked to two ripcords.

FIG. 6 shows a first compartment (51), a second compartment (52), where first compartment contains a substrate (53), such as one or more towels, e.g., a plurality of towels connected by perforations, or connectedly folded together (53), and where second compartment contains solvent (54), such as solvent containing an anti-microbial agent (54) without a fragrant compound, or a solvent containing an anti-microbial agent with a fragrant compound (54). First compartment (51) and second compartment (52) are sealed by a sealing means (56).

In some embodiments, the sealing means is configured to maintain attachment of the first compartment (51) and the second compartment (52), and creates a compartment (57) that is waterproof and airtight, and that is sandwiched in between the first compartment (51) and second compartment (52). In other embodiments, the sealing means is configured to maintain attachment of the first compartment (51) and the second compartment (52), and to create compartment (57) that is sandwiched in between the first compartment (51) and second compartment (52), where the compartment is not waterproof and not airtight. Structure number (55) indicates the overall device or system. Further aspects of sealing means are detailed above.

FIG. 6 also reveals a pull-tab (57) that is operably linked with a pull-strip (58) (or pull-string; pull-wire; pull-ribbon), where the pull-strip (58) is operably linked to one or more ripcords (59) where, as indicated, the ripcord (59) is configured to create an opening in the first compartment (51) and an opening in the second compartment (52), where the opening allows the solvent (54) to adsorb to the surface of substrate (53), to absorb into the matrix of substrate (53), or to impregnate substrate (53). The ripcord (59) is affixed to one or more points (60) (indicated by black dot) (or affixed by a continuous fixing, or by a lined fixing, or by a fixing that does not involve a point or points) of each of the first compartment (51) and to the second compartment (52), enabling the ripcord (59) to tear a frangible region or to tear a perforated region of each of the first compartment (51) and second compartment (52). In all embodiments, and without limitation, pull-tab can be hemispherical, circular, square, spherical, bead-like, and the like, or pull-tab can be omitted.

The present disclosure provides personal hygienic system, device, and method, useful for portable personal hygiene and hand cleaning. In various embodiments, the disclosure is configured to be attractive or motivational to children, adolescents, adults, women, men, or for use when traveling, or in health care or convalescent settings. Towels of the present disclosure can be made of textured, absorbent papers packed into convenient plastic compartments that contain a cleaning or sanitizing fluid.

In addition, the present device or system is configured for quick warming in a microwave oven, through solar heating, or, by any safe self-heating chemical. What is warmed or heated is pre-moistened towel, the solvent in solvent compartment, or heating towel subsequent to consumer-induced introduction of solvent into towel. "Portable" in the present context is defined as capable of being stored or transported in a satchel or handbag, e.g., Indiana Jones Satchel by Rubies (Richmond Hill, N.Y.), Classic Messenger Bag by Rothco (Ronkonkoma, N.Y.), and the like.

Warming and heating embodiments of are provided. Towel or towels, or a compartment containing towel or towels, can be warmed by any machine or radiation that is non-destructive, in use, to substrate, solvent, or compartments. Warming can be accomplished in about 5 seconds, about 10 seconds, about 15 seconds, and the like, in a consumer microwave oven, warmed by passive solar heat transfer from exposure to sunlight on a dashboard of a car, a window sill that is situated, for example, at home, at a hotel or resort, or in a classroom. In one aspect, temperature of heated towel can be measured by a sensor implanted in the towel (see, e.g., CDN DSP1 Dual-Sensing Probe Thermometer/Timer (Component Design, NW, Portland, Oreg.; Amprobe.Digital Thermometer, Type K, 2 Input (Grainger, Inc., Chicago, Ill.).

The device or system is configured so that heating results in solvent, when situated in capsule and before breaking or opening capsule, reaching a temperature of at least 37 degrees C., 40, 45, 50, 55, 60, 65, 70, 75, 80, 85, 90, 95, or at least 100 degrees C. In embodiments, heating results in breaking or rupturing of capsule, resulting in solvent being introduced into substrate. Also, the device, system, or method, is configured so that heating results in solvent, when impregnated in substrate such as towel, reaching a temperature of at least 37 degrees C., 40, 45, 50, 55, 60, 65, 70, 75, 80, 85, 90, 95, or at least 100 degrees C.

Two part exothermic heating systems are encompassed by the device, system, or methods of the present disclosure. These systems of the present disclosure can be based on a 2-part combination of: (1) Potassium thiosulfate and a catalytic amount of sodium tungstate, with (2) A mixture of potassium thiosulfate and potassium sulfite and a catalytic amount of sodium tungsate (U.S. Pat. No. 3,632,516 issued to Antonelli and Boden). The present disclosure also can include a 2-part system using: (1) Boron containing compound which reacts with a protic material in an exothermic reaction; and (2) Protic material (U.S. Pat. No. 4,110,426 issued to Barnhurst and Shumway.

Also provided, without limitation, is a 2-part system using: (1) Zeolite; and (2) Water or other aqueous solution (see, e.g. U.S. Pat. No. 6,752,998 issued to Verdrel-Lahaxe and Bui-Bertrand and incorporated expressly by reference). These patents are hereby incorporated herein in their entirety. The first compartment of the present disclosure comprises the first part of respective 2-part combination and the second compartment comprises the second part of 2-part combination. Alternatively, the first compartment of the present disclosure comprises the second part of 2-part combination and the second compartment comprises the first part of 2-part combination, respectively.

In embodiments, a device or system that comprises 2-compartments, at least 2-compartments, 3-compartments, at least 3-compartments, or a plurality of compartments, can increase stability during storage or shipping, can increase or simplify ease in manufacturing, when compared to a corresponding device or system that comprises only one compartment. For example where first compartment contains a towel that comprises a synthetic polymer, and where second compartment contains a solvent such as alcohol, acetone, ethanol, propanol, and the like, prolonged storage of the solvent with the synthetic polymer may result in deterioration of the polymer. Two-compartment or multi-compartment embodiments can prevent deactivation of anti-microbials, for example, of oxygen activated anti-microbials. Without the compartments, it is foreseeable that deactivation can occur during storage.

Two-compartment embodiments facilitate versatility in the manufacture of a wider product portfolio, for example, where a standard towel compartment can be matched with one or more of a plurality of solvent compartments. For example, the solvent compartment can include a solvent that is mainly isopropanol, where the solvent includes chlorhexidine (anti-microbial), where the solvent includes a child-oriented fragrance, where the solvent comprises an anti-anxiety fragrance (e.g., lavender), where the solvent includes both chlorhexidine and child-oriented fragrance, and the like. In embodiments, only the manufacturer can provide the finished device or system. In other embodiments, the customer is provided with a kit. The customer can assemble the kit differently, to include one or the other substrate-containing compartment, and to include one or the other solvent-containing compartment, for example, to suit the changing hygienic need or volition of the customer. In other embodiments, the capsule can be opened by consumer, and consumer can add any desired solvent, e.g., fragrant compound.

The present disclosure provides a portable 2-element system for personal hygiene. The system, composition, or method, in some embodiments, are configured to motivate children, adolescents, and adults for self-cleaning, or adults for the cleaning of infants and children, for example, at home, school, work, or while traveling. Towel embodiments are individually and conveniently packaged, and provide aesthetic qualities that are attractive to children or to other demographic groups. Methods for measuring aesthetic responses, by children as well as by adults, to fragrances are available and are readily practiced by the skilled artisan. See, for example, Mallet P, Schaal B (1998) Rating and recognition of peers' personal odors by 9-year-old children: an exploratory study. J Gen Psychol. 125:47-64; Dematte et al (2007) Olfactory cues modulate facial attractiveness. Chem. Senses. 32:603-610). Magnetic resonance imaging has correlated pleasant odors and unpleasant odors with different physiological signals (see, e.g., Popp et al (2004) Olfactory in fMRI studies: odor presentation using nasal continuous positive airway pressure. Acta Neurobiol. Exp. (Wars). 64:171-176).

Methods for measuring detection responses and threshold concentrations of fragrances, and for quantifying and standardizing fragrances are available (see, e.g., Brattolil et al (2011) Odour detection methods: olfactometry and chemical sensors. Sensors 11:5290-5322; Cometto-Muniz and Abraham (2010) Structure-activity relationships on the odor detectability of homologous carboxylic acids by humans. Exp. Brain Res. 207:75-84). A standard of 1 ou/m$^3$ is defined as the amount of odorant that, when evaporated into one cubic meter of gas air at standard conditions, causes a physiological response from a panel, e.g., detection threshold, equivalent to that of n-butanol (reference gas) evaporated into one cubic meter of neutral gas. The disclosure provides system, device, or method, for standardizing a compartment, a towel, or a capsule, that encompasses a fragrance. When the system or device is actively used by consumer, the fragrance is detectable at a pre-determined distance, where the distance is from the compartment or capsule to the consumer's nose. This distance can be pre-determined to be one inch or less, two inches or less, three inches or less, one foot or less, two feet or less, and so on.

Capsule is configured to contain an amount of solution, that when impregnated by an anti-microbial agent or cleansing agent, is effective to clean at least one hand. In embodiments, the amount of agent is sufficient to clean exactly two hands. Capsule is configured to contain an anti-microbial agent and a fragrance, or antibacterial agent and a fragrance, where the fragrance is effective to elicit a memory of cleaning hands with the towel or towels of the present disclosure, or is effective to elicit motivation to clean hands with the towel(s). In embodiments, capsule does not contain anti-microbial agent, does not contain antibacterial agent, does not contain cleanser, does not contain sanitizer, does not contain fragrance, or does not contain coloring agent or colored dye, or any combination thereof. In other embodiments, capsule does contain one or more of anti-microbial agent, antibacterial agent, cleanser, sanitizer, fragrance, or coloring agent or colored dye.

Capsule of the present system or device, can be made of materials that allow rupturing and release of solvent contents, for example, upon squeezing or twisting by consumer's fingertips, or upon brief heating in a microwave oven. Capsules that rupture are available (see, e.g., U.S. Pat. No. 6,547,468 issued to Gruenbacher et al, which is incorporated herein by reference.

In embodiments, the disclosure provides compartment that encompasses or contains one or more capsules, where compartment comprises emboss that comprises, e.g., ridges, chevrons, cross-hatchings, where emboss is configured protect capsule from accidental or unintended rupture. Also, the substrate, e.g., towel or towels, can comprise an emboss or embosses.

According to embodiments, towel is provided in one or more of a variety of sizes, such as 2 inches by 2 inches, 3 by 3, 4 by 4, 5 by 5, 6 by 6, 7 by 7, 8 inches by 8 inches, and the like, or not less than 2 inches by 2 inches, 3 by 3, 4 by 4, 5 by 5, 6 by 6, 7 by 7, or not less than 8 inches by 8 inches, and so on. In other embodiments, towels are no smaller than 5"×5" and no larger than 9"×11." The device, system, or compartment, of the disclosure can contain only one towel. Alternatively, the disclosure can contain a plurality of towels where two or more are coupled to each other by one or more perforated regions. The plurality can be 2, 3, 4, 5, 6, 7, 8, 9, 10, 11, or 12, and the like, or 2-4, 3-5, 4-6, 5-7, 6-8, 7-9, 8-10, 9-11, 10-12, and so on. Moreover, one or more towels have pleasant child-oriented fragrances, e.g., clove, peppermint, spearmint, fruit flavor, apple, lemon, cinnamon, grape, vanilla, cocoa, chocolate, and so on. The present disclosure encompasses use of scents or fragrances that enhance a mother-child relationship (see, e.g., Zaviacic et al (2009) Cosmetic perfumes vs. human pheromones (natural chemical scents) of the human female and male in signaling and performing context of their sexual behavior. Bratisl. Lek Listy. 110:472-475). Adult-oriented fragrances include, without limitation, fragrances (not including the fragrance of ethanol, if ethanol is present) of perfume, wine, beer, or a hard liquor, such as whisky, rum, or brandy.

The device or system can be especially configured for consumers that are adolescents, adults, women, and men. For example, an embodiment named, for example, "Adult Hot Towels" can include a compartment that can include fragrance of perfume, musk, narcissus, tea, coffee, wine, whiskey (Irish), whisky (Scottish), brandy, sake, shochu, and the like. Fragrances of these compounds, independent of ethanol, are mood modulators (see, e.g., Hoosain et al (2002) Potentiation of the ionotropic GABA receptor response by whiskey fragrance. J. Agric. Food Chem. 50:6828-6834; Hoosain et al (2002) Effects of tea compounds on the response of GABA (A) receptors expressed in *Xenopus* oocytes. J. Agric. Food Chem. 50:3954-3960; Hossain et al (2003) Effects of coffee compounds on the response of GABA(A) receptors expressed in *Xenopus* oocytes. J. Agric. Food Chem. 51:7568-7575; Ye et a (2011) Can odors of TCM be captured by electronic nose? The novel quality control method for musk by electronic nose coupled with chemometrics. J. Pharm. Biomed. Anal. 55:1239-1244). Dematte et al (2006) Cross-modal interactions between olfaction and touch. Chem. Senses. 31:291-300, discloses the motivational influence of narcissus scent on adults. The references indicate non-limiting sources, methods of making, and methods of measuring, chemical compositions that are adult-oriented fragrances. Another aspect of adult Hot Towels, is part of a shaving kit system, where a first compartment contains shaving cream or gel lotion, with a paper-based brush system. Second compartment contains one or more towels, or hot towels, impregnated with lubricant and antimicrobial. The paper-based application brush system is warmed or heated, the compartment containing paper-based brush system is taken out, and while pressing down on the second compartment, the warm shaving gel/cream is picked up on the brush applicator, and applied by the consumer to the face, legs, and so on.

In a consumer-changeable device, the consumer fills a port with shaving gel or shaving cream, which can lead to compartment containing towel, or it can lead to compartment that encompasses paper brush. As an alternative to shaving lotion or cream, or as an addition to shaving cream, the system contains a compartment that comprises acne medication. Green tea, green tea extract, or compounds from green tea, as well as cranberry extract, are also provided, both as adult-fragrances, as well as anti-microbial agents (see, e.g., Vance et al (2011). Evaluation of the antimicrobial efficiency of green tea extract (egcg) against *streptococcus pyogenes* in vitro. Biomed. Sci. Instrum. 47:177-182). Other embodiments include, e.g., anti-itching compound, hemorrhoidal treatment compound, feminine anti-odor compound (e.g., Bidet Hot Towels), or cosmetic removing solvent, or body wash suitable for traveling or camping.

Anxiety-reducing Hot Towels are also provided. Without intending any limitation, an embodiment called, "Airline Hot Towels," includes a compartment that encompasses or contains a fragrant compound shown to reduce anxiety, where this fragrant compound can be, for example, lavender or heliotropin (see, e.g., Field et al (2005) Lavender fragrance cleansing gel effects on relaxation. Int J Neurosci. 115:207222; Redd et al (1994) Fragrance administration to reduce anxiety during MR imaging. J. Magn. Reson. Imaging. 4:623-626). Anxiety, and the mitigating influence of aromas or fragrances on anxiety, can be measured by MRI, EEG (electroencephalography), or heart rate. Field et al, supra, established a correlation between decreased heart rate and increased relaxation, in studies of human subjects exposed to lavender fragrance. Another embodiment is, Etiquette Towels, the package contains a design, an emboss, or a design and emboss, where the design or emboss can contain symbol, picture, or inscription representing proper etiquette, e.g., a picture of Queen Victoria, or of Emily Post (see, e.g., Hughes (1998) The Writer's Guide to Everyday Life in Regency and Victorian England from 1811-1901. Writer's Digest Books; Post (2011) Emily Post's Etiquette, 18$^{th}$ ed., William Morrow).

According to one or more embodiments, towel configurations can have a compartment that holds a pre-filled capsule or sachet, or provide a satellite port which could be filled with a solvent, or mixture of solvents. The satellite port can be used to direct solvent to a compartment that contains a substrate, e.g., a towel or towels, to a compartment that contains a solvent, e.g., anti-microbial agent, fragrance, dye, or any combination thereof, or to a compartment that contains a towel that is already impregnated with one or more solvents. Alternatively, one port can be used to direct solvent to a substrate compartment and also to a solvent compartment. Also, two separate ports can be used to direct solvent separately to substrate compartment and to solvent compartment.

According to embodiments, the present disclosure provides a method for cleansing hands comprising: opening a first compartment that is a water-impermeable package, where the package comprises at least one towel, where the towel optionally is impregnated with an anti-microbial or anti-bacterial solvent, opening a second compartment which comprises solvent, where the opening is configured to direct or allow impregnation of the towel with the solvent, and impregnating the towel with solvent, warming the solvent either before or after opening the first or the second compartment; applying the towel to the skin to remove or kill germs on the skin or mucosal surfaces; and discarding the towel after one time use.

The disclosure likewise encompasses systems, devices, or methods that use a substrate that is disposable, that is reusable, or a substrate that cannot be reused. Without limitation, a re-usable substrate is one that can be washed, recycled, cleaned, or otherwise restored to substantially its initial capability for cleansing, without substantial degradation of the structural and functional characteristics of the substrate, e.g., without shredding or ripping of a towel.

Capsule can, without implying any limitation, contain a liquid, a powder, a gel, a slurry, crystals, soluble beads, or any combination thereof. Capsule can be encompassed by, or stored within, a first compartment, a second compartment, a substrate compartment, a substance compartment, or a plurality of capsules can be encompassed by, or stored within, any combination of these. In embodiments, capsule contains anti-bacterial, anti-microbial, fragrance, anti-microbial and fragrance, or anti-bacterial and fragrance, and the like. Capsule can be broken by physical force, for example, by squeezing pressure from the consumer or user, by way of exposure to microwave radiation, or by way of heat radiation.

By keeping the active ingredient separate from the wetted medium or by keeping the active ingredient and the wetted medium housed in separate compartments, rather than mixed together in one compartment, physical durability is increased, and shelf life or expiration date of said components is increased. The proprietary nature of all natural biocide is most effective when combined with the substrate or towel just before use. The capsule or sachet packet will be physically broken while dispensing the active ingredient into the towel or towelette; the capsules/sachets can also be opened and burst automatically when the compartment containing one or more towels is warmed in the microwave oven, or electric warmer, e.g., electric hot tray. The capsules will also contain a coloring additive which can be dispersed into the towel when activated giving a visual confirmation the capsule and towel have been activated.

Depending upon the target market and customer for the specific substrate, for example, one or more towels, each towel can contain a unique essence, aroma, or fragrance for the consumer, for example, Children's Hot Towels would contain one or more of the following fragrant compounds, e.g., fruit, bubble gum, caramel, watermelon, caramel popcorn; General Wipes for adult population for personal care use would contain the following fragrances: spice essence. The present disclosure is suited for collaborations or agreements with child-oriented children's restaurants and theme parks, such as Chuck E. Cheese®, McDonald's®, The Walt Disney Company®, and the like, and with child-oriented merchandise companies, such as Mattel®, Hello Kitty®, Marvel®, Paul Frank®, and the like. In embodiments, the first compartment can contain one fragrant compound, such as strawberry, and the second compartment can contain a different fragrant compound, such as banana.

The disclosure provides a towel, or hot towel, that comprises a fragrant compound, wherein the fragrant is impregnated in the substrate, occurs as part of a coating on the substrate, or is incorporated in bulk during manufacture of the substrate, without intending any limitation. The present device, system, or method, are configured so that fragrance can be detected by a child where the towel is located about 5 inches, about 10 inches, about 15 inches, about 20 inches, from consumer's nose. The disclosure provides a device that serves as a cue to the memory, where the cue stimulates the child to use the towel to wipe his or her own hands. It has been demonstrated that odors are equivalent to other stimuli, for example pictures or diagrams, tactile cues placed in one's hand, or verbal cues, in eliciting memories (Herz (1998) Are odors the best cures to memory? Ann. N.Y. Acad. Sci. 855: 670-674; Herz et al (2004) Neuroimaging evidence for the emotional potency of odor-evoked memory. Neuropsychologia 42:371-378).

Tests for assessing the ability of odors to elicit memories, or the ability of odors to elicit motor activities, are available (see, e.g., Psychological tests for recall, including recall that is prompted by fragrances, are available (Smith et al (2011) Informed consent in trauma: Does written information improve patient recall of risks? A prospective randomised study. Injury. July 20 [epub ahead of print]; Jehl and Murphy (1998) Developmental effects on odor learning and memory in children. Ann. N.Y. Acad. Sci. 855:632-634; Seo et al (2010) Cross-modal integration between odors and abstract symbols. Neurosci. Lett. 478:175-178; Rossi (2008) Distinct olfactory cross-modal effects on the human motor system. PLoS 3:e1702).

What is provided is a device and method for eliciting recall of a procedure for using towel for cleaning one's hands, comprising a towel that comprises a fragrance detectable by a child, or comprising a first compartment that comprises a towel and a second compartment that comprises a fragrant compound wherein in use the fragrant compound is absorbed by the towel, and where the fragrant compound that is absorbed by the towel is detectable by a child, where the child associates the fragrance with the child's own use of the towel to clean the child's own hands.

According to embodiments, a wet towel apparatus for motivating hand cleaning, comprising in combination: at least an enclosed towel member; and a formulation effective for at least one of organicidal, germicidal, and bacteriocidal action for usage.

According to embodiments, the system and method of the present disclosure includes an anti-bacterial agent comprising a solvent, a natural oil, an herbal extract, a natural aromatic compound, traditional natural products derived from foods, and other compounds, which are either synthetic or prepared from natural sources, comprising at one or more of carvacrol, which is extracted from oil of thyme and has an oregano aroma, eugenol, which has a clove aroma, and thymol, also from oil of thyme provided by (Garcia-Garcia, et al (2011) J. Food Sci. 76:M95-M100; Devi, et al. (2010) J. Ethnopharmacol. 130:107-115); celery seed extract, which has been used in herbal medicine (Zhou, et aol (2009) J. Pharm. Pharmacol. 61:1067-1077); black tea extract (Tiwari, et al (2005) Indian J. Med. Res. 122:80-84); grape kernel extract (Thuille, et al (2003) Int. J. Hyg. Environ. Health 206:217-221); peppermint oil or orange oil (Schelz, et al (2006) Fitoterapia 77:279-285); organic solvents such as acetone, ethanol, propanol, mixtures thereof, and aqueous solutions thereof, (Lacey (1968) Br. J. Exp. Pathol. 49:209-215; Snell (1954) Appl. Microbiol. 2:174-175; Kampf, et al (2008) Ann. Clin. Microbiol. Antimicrobials 7:2 (6 pages)); polyphenols from apple skin have been shown to be antibacterial (Du, et al (2011) J. Food Sci. 76:M149-155); any mixture of synthetic versions of natural compounds, synthetic derivatives of compounds from the above sources, mixtures of extracted natural compounds, synthetic compounds, solvents alone, and one or more solvents in combination with a natural compound. The present disclosure also encompasses the oils and fragrances identified by U.S. Publ. No. 2011/0042257 of Mueller, et al, which is hereby incorporated herein by reference.

The present disclosure includes, without limitation, methods and compositions for heating, including microwave heating, solar heating, and heat-producing compositions such as exothermic systems that use calcium oxide or calcium chloride (see, e.g., U.S. Pat. No. 3,957,472 issued to Donnelly; U.S. Pat. No. 4,425,251 issued to Gancy, or U.S. Pat. No. 4,573,447 issued to Thrash et al).

In another aspect, the disclosure provides a frangible seal that allows communication between two compartments, where the frangible seal can be broken by manual twisting, pressing, squeezing, and the like. What is contemplated is a system, device, and method that does not transfer a substance (fluid, liquid, solvent, fragrance, antimicrobial, dye, and the like) to a substrate, by way of a pipe, a conduit, a roller, and the like.

In one aspect, the disclosure provides a first compartment that is configured to comprise said substance, and a second compartment that is configured to comprise said substrate, where the first compartment is substantially adjacent to the second compartment, or where the first and second compartments are situated coaxially to each other. In coaxial embodiments, the substance containing compartment can be distal and the substrate-containing compartment can be proximal, or the substrate-containing compartment can be proximal and substance-containing compartment can be distal. Rolled embodiments are also provided, that is, where a substance compartment and substrate compartment are wrapped in the spiraling manner of a typical cinnamon bun.

The device and method of the present disclosure can be activated and/or opened, where a string is positioned near or in contact with a compartment wall, where pulling string provokes communication between substance compartment and substrate compartment, or where a notch is positioned on an edge of present device, where user grabs one portion of edge on each side of notch, pulls edges in opposite directions, resulting in the stressed notch guiding a tear, where the tear provokes communication between substance compartment and substrate compartment. Perforation embodiments are provided, where user tears edge along perforations, where the resulting tear provokes communication between substance compartment and substrate compartment.

In one embodiment, the first and second compartments are configured to allow direct passage of the substance to the substrate, while in another embodiment, the substance passes through an intermediary, such as a gauze, foam, web, or space containing a vacuum or air, before passing into the substrate. In embodiments, the device, system, and method, includes an intermediary, or excludes an intermediary.

In some aspects, the substrate compartment is tillable by consumer with a substrate, for example, with a white towel, a colored towel, a scented towel, or a non-scented towel, while in other aspects, the substrate compartment is only tillable by manufacturer and cannot be filled by consumer. In some aspects, the substance compartment is tillable by consumer with a substance, for example, with an antibacterial agent, a cleansing solvent, or an anti-fungal agent, while in other aspects, the substrate compartment is only tillable by manufacturer and cannot be filled by consumer.

In a first aspect, the substrate can be impregnated with substance prior to exposure of substrate to the outside environment, e.g., to the visual field of the consumer. What is encompassed are embodiments that exclude this first aspect. In a second aspect, the substrate can be impregnated with substance at about the same time as exposure of the substrate to the outside environment. Also encompassed are embodiments that exclude this second aspect. In a third aspect, the substrate can be impregnated with substance substantially after exposure of the substrate to the outside environment. Also encompassed, are embodiments that exclude this third aspect.

In one aspect, substrate compartment contains a single towel, two towels, three towels, or more towels, where the towels are not perforated and are not attached, or where the towels are perforated and are detachably attached. In one aspect, the towel is dry, impregnated with an aqueous solution, with an organic molecule, with an oil, with a solution that contains less than 10% water, less than 5% water, or less than 2% water, with a non-aqueous solvent, impregnated with a solvent that is a mixture of water and an organic molecule. The organic molecule can be, e.g., ethanol, acetone, propanol, an herbal oil, a plant oil, an oil from an edible crop or edible plant, or any mixture thereof.

Exfoliating agents are encompassed, for example particles derived from ground or powdered watermelon seeds, peach seeds, walnut shells, apricot seed, bentonite, volcanic ash, diatomaceous earth, pumice, and the like.

The disclosure provides compositions that can improve motivation of consumers, especially children, to use the device, system, or method of the present disclosure, where these compositions take the form of substances that are otherwise used as flavorings or fragrances in products marketed for children, such as products that are soda pop or chewing gum. These compositions include exfoliating agents derived from watermelon seeds or peach seeds. These compositions also include, e.g., grape kernel extract, peppermint oil, spearmint oil, or compounds derived from apples. Labeling of the product with terms such as watermelon, peach, grape, peppermint, or apples, or detection of fragrance or taste by the consumer, can increase motivation to use the present device, system, or method. It has been determined that games and art projects, for example, can improve a child's motivation to adhere to good health practices (see, e.g., Darnaud and Dato (2009) Health education in schools in Argentina: an art contest as motivating activity. Rev. Panam. Salud. Publica. 25:181187; Jabre (1981) Innovative approaches in nutrition education in the Pacific region. Int. J. Health Educ. 24:95-101.

Compartment is configured to be opened, by the consumer, by way of one or more pull-tabs. The one or more pull-tabs is operably linked with an adhesive strip that seals the substrate compartment, the solvent compartment, or both the substrate compartment and solvent compartment. Separate pull-tabs can be operably linked with a first adhesive strip that seals the substrate compartment and a second adhesive strip that seals the solvent compartment. The disclosure is configured so that dislodging or peeling adhesive strip from substrate compartment provides an opening that is configured for solvent to impregnate the substrate, e.g., towel, within substrate compartment. Moreover, the disclosure is configured so that dislodging or peeling adhesive strip from solvent compartment releases solvent, e.g., anti-microbial, fragrance, colored dye, and the like, where the released solvent can impregnate the substrate.

In other embodiments, the one or more pull-tabs can be operably linked with a thread, cord, string, or ribbon, configured to introduce a tear or rip in the substrate compartment, solvent compartment, or both. In still other embodiments, the one or more pull-tabs is configured to be operably linked with a zipper or zipping mechanism, configured to open the substrate compartment, solvent compartment, or both. The adhesive seal maintains adhesion of sealing strip to a pre-determined opening slit in substrate compartment or solvent compartment, where the adhesive seal impairs or prevents solvent from evaporating from the substrate compartment, that is, where substrate compartment contains a towel that is pre-moistened, or from evaporating from solvent compartment. Graspable tabs, adhesive strips, adhesive seals, tear bands, in consumer products are available. See, e.g., U.S. Pat. No. 8,051,979 issued to Smith et al; U.S. Pat. No. 7,967,140 issued to Grossman; U.S. Pat. No. 5,114,507 issued to Bellamah et al. Each of these patents is incorporated herein by reference.

The pull-tab is operably linked with a port. The port where the pull-tab is pulled out exposes the wetted towel (contained in substrate compartment) is adapted to be a built-in safety and heat release mechanism. Where the towel or towels in the substrate compartment become too hot, excess heated air, or excess vapor or steam, will be released and vented. Venting is by way of a safety heat release port.

In embodiments, substrate compartment and solvent compartment of the disclosure are configured to be in substantial contact with each other, permitting issue of solvent, anti-microbial, or fragrance, directly from one compartment to the other, when compartments are opened, where embodiment exclude one or more channels, and excludes one or more passages between the two compartments, and excludes an egress neck. In an alternative embodiment, substrate compartment, prior to opening seal of substrate compartment, does not contain any flowable substance (e.g., powder, slurry, liquid, gel), or contains an absorbent composition impregnated with a liquid where the absorbent composition prevents the liquid from being flowable.

Pull-tab can be configured for stripping the adhesive strip away from the compartment, revealing a pre-formed slit or opening in the compartment, where the opening allows issue of a solvent or fluid into the compartment or out of the compartment. Alternatively, the adhesive strip itself can be perforated, scored, or provided with a frangible seal or joint, along the longitudinal axis is the adhesive strip, where the pull-tab is configured to rip open the perforations, thereby exposing the slit. In some aspects, the adhesive strip can be used only one time, and is not re-sealable.

Adhesives, adhesive tapes, films, pouches, sachets, and the like are available. Publications, suppliers, and manufacturers include, e.g., 3M Adhesives and Tapes. Design and Production Guide for Application Success (100 pages) 3M Corporation, St. Paul, Minn.; Soroka (2009) Fundamentals of Packaging Technology, $4^{th}$ ed. DEStech Publications, Lancaster, Pa.; Luo et al (2010) A thermally responsive, rigid, and reversible adhesive. Polymer 51:1169-1175; Amcor Limited, Melbourne, Australia; Impact Mfg., City of Industry, Calif.

The present inventor has discovered that by providing an elegantly simple system for portable personal cleansing agents and sanitary agents, numerous needs can be addressed. According to embodiments, the present disclosure could be gamma ray sterilized for added efficacy, and the closed system capsule or sachet is broken to disperse the additive on to the towel. The disclosure involves selected ranges of a 2-part system designed to be attached to an extension handle for floor, wall, and ceiling cleaning, or floor polishing, or counter top disinfection. Disclosure encompasses a range of materials, including natural fibers, such as those from cotton, sugar cane, bamboo trees, and synthetic fibers or sheets, such as those made from plastic polymers, e.g., polyester.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation as to encompass all such modifications and similar structures. The present disclosure includes any and all embodiments of the following claims. It should also be understood that a variety of changes may be made without departing from the essence of the disclosure. Such changes are also implicitly included in the description. They fall within the scope of this disclosure. It should be understood, this disclosure is intended to yield a patent covering numerous aspects of the invention both independently and as an overall system, in both method and apparatus modes.

Further, each of the various elements of the disclosure and claims may also be achieved in a variety of manners. This disclosure should be understood to encompass each such variation, be it a variation of an implementation of any apparatus implementations, a method or process implementations, or merely a variation of any element of these.

Particularly, it should be understood that as the disclosure relates to elements of the invention, the words for each element may be expressed by equivalent apparatus terms or method terms—even if the function or result remains the same. Such equivalent, broader, or even more generic terms should be considered to be encompassed in the description of each element or action. Such terms can be substituted where desired, to make explicit, the implicitly broad coverage to which this invention is entitled.

It should be understood that all actions may be expressed as a means for taking that action or as an element which causes that action. Similarly, each physical element disclosed, should be understood, to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular exemplary implementations, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim which would have literally encompassed such alternative exemplary implementations.

Further, the use of the transitional phrase "comprising" is used to maintain the "open-end" claims herein, according to traditional claim interpretation. Thus, unless the context requires otherwise, it should be understood the term "compromise" or variations such as "comprises" or "comprising", are intended to imply the inclusion of a stated element or step or group of elements or steps but not the exclusion of any other element or step or group of elements or steps. Such terms should be interpreted in their most expansive forms so as to afford the applicant the broadest coverage legally permissible.

What is claimed is:

1. A portable system for personal hygiene that comprises, in combination,
   a first compartment configured for containing at least one substrate,
   a second compartment configured for containing a solvent,
   wherein one or both compartments comprise a frangible region that can be opened or ruptured,
   wherein opening or rupturing the frangible region is adapted to allow the solvent to contact and absorb into the at least one substrate, where maintaining the frangible region is adapted to prevents the solvent from contacting the at least one substrate,
   and further comprising a member that is manually operable by user that opens or ruptures the frangible region,
   wherein the first compartment contains a first chemical reagent of an exothermic composition, and the second compartment contain a second chemical reagent of the exothermic composition, wherein combination of the two reagents generates heat, wherein the frangible region is configured, when opened or ruptured, to allow combination of the two reagents to create an exothermic reaction, and wherein at least one of the compartments contains a solvent, where the exothermic reaction increases the temperature of the solvent, and
   wherein the first compartment comprises a third compartment, or wherein the second compartment comprises a fourth compartment, wherein the third compartment is configured for containing the first chemical reagent, and the fourth compartment is configured for containing the second chemical reagent.

2. The system of claim 1, wherein the first compartment contains at least one substrate.

3. The system of claim 1, wherein the substrate is at least one absorbent towel.

4. The system of claim 1, wherein the first compartment does not contain a substrate.

5. The system of claim 1, wherein the second compartment contains at least one solvent.

6. The system of claim 1, wherein the solvent comprises water or an organic solvent, or a mixture of water and an organic solvent.

7. The system of claim 1, wherein the solvent comprises at least one fragrant compound, at least one anti-microbial compound, at least one dye, a combination of fragrant compound and anti-microbial compound, or any combination thereof.

8. The system of claim 1, wherein the solvent comprises at least one fragrant compound that is a child-oriented fragrant compound or an adult-oriented fragrant compound.

9. The system of claim 1, wherein the second compartment does not contain a solvent.

10. The system of claim 1, where the second compartment comprises a capsule, where the capsule is configured for containing the solvent.

11. The system of claim 1, wherein the system is configured so that, in use, the first chemical reagent, the second chemical reagent, and the exothermic combination do not touch or mix with the solvent and do not touch or absorb into the substrate.

12. The system of claim 1, wherein the second compartment that is configured for containing a solvent comprises at least one capsule, wherein the at least one capsule contains essentially all of the solvent that is comprised by the second compartment.

13. The system of claim 1, wherein the first compartment, second compartment, or both first and second compartments, comprise an adhesive strip or pull-cord that is operably linked to the frangible region, wherein in use, the adhesive strip or pull-cord opens or ruptures the frangible region.

14. The system of claim 1, wherein the first compartment and the second compartment are configured to define a chamber that is entirely in between the first and second compartments, wherein in use opening or rupture of the frangible region results in solvent leaving the second compartment for the chamber, and solvent in the chamber entering the substrate compartment.

15. A method for cleaning hands, comprising opening or rupturing the frangible region of the system of claim 1, allowing solvent to contact and absorb into the at least one substrate, withdrawing the at least one substrate from the system, and applying or wiping the at least one substrate to at least one hand that is in need of cleaning.

16. A method for eliciting a recall of a procedure for cleaning hands, or for motivating a child to clean his or her hands, comprising the method of claim 15, wherein the solvent comprises a child-oriented fragrant compound,
   wherein, in use, the fragrant compound is absorbed by the substrate, and wherein, in use, the fragrant compound that is absorbed by the substrate is detectable by a child holding the substrate at a distance of less than three inches from the child's own nose.

17. The method of claim 16, wherein the eliciting recall is measurable by a first test, and the motivating a child is measurable by a second test, wherein the first test or second test are one of a psychological test, behavioral test, electroencephalogram test, or brain magnetic resonance imaging (MRI) test.

18. The method of claim 15, further comprising warming the solvent prior to contacting or absorbing the solvent to the at least one substrate prior to the cleaning of hands, or warming the solvent-absorbed in the at least one substrate prior to the cleaning of hands.

* * * * *